(12) United States Patent
Miyabe et al.

(10) Patent No.: US 8,021,439 B2
(45) Date of Patent: Sep. 20, 2011

(54) TWO-PART HAIR DYE

(75) Inventors: Hajime Miyabe, Tokyo (JP); Takashi Matsuo, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/083,887

(22) Filed: Apr. 11, 2011

(65) Prior Publication Data

US 2011/0186071 A1 Aug. 4, 2011

Related U.S. Application Data

(63) Continuation of application No. 12/739,471, filed as application No. PCT/JP2008/003033 on Oct. 24, 2008, now Pat. No. 7,938,864.

(30) Foreign Application Priority Data

| Oct. 24, 2007 | (JP) | 2007-276739 |
| Oct. 24, 2007 | (JP) | 2007-276740 |
| Oct. 24, 2007 | (JP) | 2007-276742 |
| Oct. 24, 2007 | (JP) | 2007-276809 |

(51) Int. Cl.
*A61Q 5/10* (2006.01)

(52) U.S. Cl. .......... 8/405; 8/431; 8/457; 8/526

(58) Field of Classification Search .......... 8/405, 431, 8/457, 526
See application file for complete search history.

(56) References Cited

U.S. PATENT DOCUMENTS

| 5,635,461 | A | 6/1997 | Onitsuka et al. |
| 5,716,626 | A | 2/1998 | Sakurai et al. |
| 2004/0213752 | A1* | 10/2004 | Fujinuma et al. ............ 424/70.1 |
| 2010/0126522 | A1 | 5/2010 | Fujinuma et al. |
| 2010/0126523 | A1 | 5/2010 | Fujinuma et al. |
| 2010/0316583 | A1 | 12/2010 | Fujinuma et al. |

FOREIGN PATENT DOCUMENTS

| JP | 8 85800 | 4/1996 |
| JP | 8-225441 | 9/1996 |
| JP | 8 259426 | 10/1996 |
| JP | 9 136818 | 5/1997 |
| JP | 10 236929 | 9/1998 |
| JP | 10-273431 | 10/1998 |
| JP | 2002 284655 | 10/2002 |
| JP | 2003-277230 | 10/2003 |
| JP | 2004 339216 | 12/2004 |
| JP | 2006 124279 | 5/2006 |
| JP | 2007 314524 | 12/2007 |
| WO | WO/2010/103795 | 9/2010 |
| WO | WO/2010/103796 | 9/2010 |

OTHER PUBLICATIONS

Notice of Submission of Publications issued Oct. 27, 2009 in JP Application No. 2008-274238 (With English Translation).

* cited by examiner

*Primary Examiner* — Eisa Elhilo

(74) *Attorney, Agent, or Firm* — Oblon, Spivak, McClelland, Maier & Neustadt, L.L.P.

(57) ABSTRACT

A two-part hair dye including a first part containing an alkali agent, a second part containing hydrogen peroxide, and a non-aerosol foamer vessel to discharge in the form of foam a liquid mixture of the first part and the second part, wherein the liquid mixture contains anionic surfactant (s) selected from the following components (A): (A) a carboxylic type anionic surfactant selected from salts of a $C_8$ to $C_{22}$ fatty acid; and wherein the content of component (A) in the first part or the second part is 0.1 to 30% by mass.

37 Claims, No Drawings

TWO-PART HAIR DYE

CROSS-REFERENCE TO RELATED APPLICATIONS

The present application is a continuation of U.S. Ser. No. 12/739,471, filed Apr. 23, 2010, which is a National Stage (371) of PCT/JP08/003033, filed Oct. 24, 2008, which claims priority to JP 2007-276740, filed Oct. 24, 2007, JP 2007-276739, filed Oct. 24, 2007, JP 2007-276809, filed Oct. 24, 2007, and JP 2007-276742, filed Oct. 24, 2007.

FIELD OF THE INVENTION

The present invention relates to a two-part hair dye.

BACKGROUND OF THE INVENTION

Conventionally, hair dye compositions in a form of liquid or cream have been broadly used, however it is not easy to apply them to hair evenly. When a consumer herself applies a dye to her own hair root or the back of her own head, not only skills in a hair blocking or two-mirror technique and the like are required, but also a careful manipulation is required for uniform application.

To simplify the dyeing procedure, it has been proposed to discharge the dye in the form of foam, and two-part aerosol dyes and one-part non-aerosol dyes have been known. Concerning the two-part aerosol dyes, there have been the following problems that: a mixture ratio of the first part and the second part is not constant and uneven bleaching or uneven dyeing is likely to take place; a high pressure metallic vessel may be corroded by oxidation by hydrogen peroxide; and the internal pressure of the high pressure vessel may rise excessively by decomposition of hydrogen peroxide. Concerning the one-part non-aerosol dyes, there have been the following problems that: due to non- or weak bleaching ability, it is difficult to change a color tone substantially with a single dyeing operation; and to dye to a brilliant color tone, it is required to leave the dye on the hair for a long period of time after application or repeat the operation thereby making the dyeing operation rather cumbersome.

On the other hand, two-part hair dye compositions to be discharged in the form of foam from a non-aerosol foamer vessel have been proposed (Patent Document 1 and Patent Document 2). By discharging a liquid mixture of the first and second parts from the non-aerosol foamer vessel in the form of foam, the mixture ratio thereof can be more constant than the conventional two-part aerosol dyes, and sufficient bleaching ability and dyeability compared with the conventional one-part non-aerosol dyes can be obtained.
Patent Document 1: JP-A-2004-339216
Patent Document 2: JP-A-2006-124279

SUMMARY OF THE INVENTION

The present invention provides a two-part hair dye including a first part containing an alkali agent, a second part containing hydrogen peroxide and a non-aerosol foamer vessel to discharge in the form of foam a liquid mixture of the first part and the second part, wherein the liquid mixture contains anionic surfactant(s) selected from the following components (A1) to (A3):
(A1) a carboxylate type anionic surfactant;
(A2) a sulfonate type anionic surfactant; and
(A3) a phosphate type anionic surfactant.

The present invention further provides a two-part hair dye including a first part containing an alkali agent, a second part containing hydrogen peroxide and a non-aerosol foamer vessel to discharge in the form of foam a liquid mixture of the first part and the second part, wherein the liquid mixture contains the following components (A4) and (A5):
(A4) an ionic surfactant; and
(A5) a fatty acid alkanolamide.

The present invention further provides a method for dyeing hair, including the steps of discharging in the form of foam the aforedescribed liquid mixture in the two-part hair dye from a non-aerosol foamer vessel; applying the foam to the hair; and foaming again the foam on the hair.

DETAILED DESCRIPTION OF THE INVENTION

The present invention relates to a two-part hair dye in the form of foam superior in preservation stability, ease of application to the hair and low irritation to the scalp while maintaining the advantages of good bleaching ability and dyeability according to Japanese Patent 1 and Japanese Patent 2, and to a two-part hair dye in the form of foam superior in a foaming property also at a lower temperature and resistant to drip from the application of the liquid mixture to the hair until being washed away.

The present inventors have discovered that with a non-aerosol two-part hair dye by use of a specific surfactant in the liquid mixture of the first and second parts the aforedescribed object can be achieved, thereby accomplishing the present invention.

According to the present invention, the liquid mixture of the first and second parts can be discharged in the form of foam and applied to the hair evenly and easily. The discharged foam of the liquid mixture is compatible to the hair so that a large amount can be applied; is free from irritation to the scalp, spattering of the liquid, or dripping of the liquid; and has sufficient bleaching ability or dyeability. Consequently, the two-part hair dye of the present invention can realize easily and comfortably a uniform and less uneven bleaching or dyeing.

The liquid mixture discharged in the form of foam by gas/liquid mixing using the non-aerosol foamer vessel can reach easily the hair root without forming a liquid pool spreading appropriately over a part of the hair to be bleached or dyed. Consequently, extreme blonding at the hair root or uneven bleaching or dyeing caused by unevenness in the coated amount of the liquid mixture does not occur as in the case of a conventional liquid or cream type dye. Therefore the two-part hair dye of the present invention can be applied to the hair at new growth areas near a part or a face line, so that color difference between the new growth area and previously dyed area can be eliminated to achieve a natural finish. Further, since the liquid mixture can be applied to the hair in an appropriate amount, damages to the hair can be reduced.

If the anionic surfactant selected from the components (A1) to (A3), or the components (A4) and (A5) as surfactants are contained in the first part containing the alkali agent, or in the second part containing hydrogen peroxide, the preservation stability is good and preferable quality of foam can be maintained for a long time.

<Definitions>

A hair means herein a hair fixed on the head, and a hair separated from the head, such as a wig or a tress, is excluded. Although there is no restriction on a hair, from a doll's hair to an animal hair, a human hair is preferable.

Herein a simple expression of a "two-part dye" refers to a broad concept including also a non-aerosol foamer vessel.

Further, the two-part dye refers to a concept including both a hair dye containing a dyestuff, and a bleach not containing a dyestuff. Furthermore, a "liquid mixture in the two-part dye" means the liquid mixture of the first and second parts. A method for dyeing the hair refers to a concept including a method for bleaching the hair.

<Alkali Agent>

As the alkali agent to be contained in the first part, for example, ammonia, an alkanolamine such as ethanolamine, sodium hydroxide and potassium hydroxide can be used. Further, as a buffer, an ammonium salt, such as ammonium hydrogencarbonate and ammonium chloride, and a carbonate, such as potassium carbonate and sodium hydrogen carbonate may be appropriately added.

The pH of the liquid mixture of the first and second parts of the two-part hair dye of the present invention is preferably 8 to 11, more preferably 9 to 11, and the amount of the alkali agent for use is adjusted appropriately so that the pH of the liquid mixture fall within the above range.

<Hydrogen Peroxide>

The hydrogen peroxide content in the second part is preferably 1 to 9% by mass and more preferably 3 to 6% by mass, and the hydrogen peroxide content in the liquid mixture of the first and second parts is preferably 1 to 6% by mass and more preferably 2 to 5% by mass. While, the pH of the second part is preferably 2 to 6 and more preferably 2.5 to 4, in order to prevent decomposition of the hydrogen peroxide.

<Anionic Surfactant to be Selected from (A1) to (A3)>

By use, as a surfactant, of an anionic surfactant selected from (A1) a carboxylate type anionic surfactant; (A2) a sulfonate type anionic surfactant; and (A3) a phosphate type anionic surfactant; a two-part hair dye in the form of foam superior in preservation stability, ease of application to the hair and low irritation to the scalp while exerting good bleaching ability and dyeability can be obtained.

[(A1) Carboxylate Type Anionic Surfactant]

A foaming agent is added to either or both of the first part and the second part so that stable foam is easily generated by mixing the liquid mixture in the two-part hair dye with air by a foam discharge means of the foamer vessel. As the foaming agent a carboxylate type anionic surfactant is added in order to generate the foam easy to apply and compatible to the hair.

Examples of the carboxylate type anionic surfactant include an N-acyl amino acid salt, an N-acyl-N-alkylamino acid salt, an amide type N-acyl amino acid salt, an ether carboxylic acid salt, a fatty acid salt, and a salt of an alkyl succinate or an alkenyl succinate.

Thereby, examples of an amino acid residue for the N-acyl amino acid salt include glutamic acid and aspartic acid, and examples of an amino acid residue for the N-acyl-N-alkylamino acid salt include glutamic acid, glycine and β-alanine. Examples of an alkyl group for the N-acyl-N-alkylamino acid salt include a methyl, ethyl, propyl and isopropyl group. Examples of an acyl group include a lauroyl, myristoyl and palmitoyl group, and examples of the salt thereof include a sodium, potassium, lithium, ethanolamine, diethanolamine and triethanolamine (hereinafter abbreviated as "TEA") salts. Specific preferred examples include for the N-acyl amino acid: N-lauroyl glutamic acid, N-myristoyl glutamic acid and N-cocoyl glutamic acid, and for the N-acyl-N-alkylamino acid: N-lauroyl-N-isopropyl glycine, N-lauroyl-sarcosine, N-myristoyl-sarcosine, N-palmitoyl-sarcosine and N-lauroyl-N-methyl-β-alanine.

Examples of the amide type N-acyl amino acid salt include an amide type N-acyl amino acid salt represented by the following general formula (1):

$$R^1CON(CH_2)_nCOOM^1 \qquad (1)$$

wherein $R^1CO$ represents a $C_{10}$ to $C_{22}$ acyl group; "n" represents an integer of 1 or 2; and $M^1$ represents in the case "n" is 1, sodium, potassium or an alkanolammonium, and in the case "n" is 2, potassium or an alkanolammonium.

For the amide type N-acyl amino acid salt, the acyl group represented as $R^1CO$ in the general formula (1) is preferably linear, and preferred specific examples thereof include a caprynoyl group, a lauroyl group and a myristoyl group.

Examples of the ether carboxylate salt include a polyglyceryl alkyl ether acetate salt and an ether acetate salt represented by the following general formula (2):

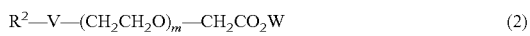

$$R^2-V-(CH_2CH_2O)_m-CH_2CO_2W \qquad (2)$$

wherein $R^2$ represents a $C_7$ to $C_{19}$ linear or branched alkyl or alkenyl group; V represents —O— or —CONH—; W represents a hydrogen atom, an alkali metal, triethanolamine or ammonium; and "m" represents a number between 1 and 20.

For the ether acetate salt, the carbon number of $R^2$ is preferably 11 to 15. The "m" is preferably 3 to 15, and more preferably 6 to 12. Specific examples include polyoxyethylene (10) lauryl ether acetic acid (in the general formula (2), $R^2=C_{12}H_{25}$, V=—O—, m=10), polyoxyethylene (8) myristyl ether acetic acid (in the general formula (2), $R^2=C_{14}H_{29}$, V=—O—, m=8), laurylamide polyoxyethylene (6) ether acetic acid (in the general formula (2), $R^2=C_{11}H_{23}$, V=—CONH—, m=8), laurylamide polyoxyethylene (10) ether acetic acid (in the general formula (2), $R^2=C_{11}H_{23}$, V=—CONH—, m=10). The degree of neutralization thereof is preferably 60 to 120%, and as the counter ion W an alkali metal is preferred, with potassium being more preferred.

Examples of the fatty acid salt include a basic salt of a $C_8$ to $C_{22}$ fatty acid. Specific examples include basic salts of a single fatty acid, such as lauric acid, myristic acid, palmitic acid, isostearic acid and oleic acid, as well as a fatty acid mixture, such as coconut oil fatty acid and tallow fatty acid. Thereby, examples of the salt include inorganic basic salts such as sodium or potassium, an ammonium salt, alkanolamine salts, such as an ethanolamine salt, a diethanolamine salt, a triethanolamine salt, 2-amino-2-methylpropanol and 2-amino-2-methylpropanediol, and basic amino acids, such as lysine and arginine.

Examples of an alkyl group or an alkenyl group in the salt of an alkyl succinate salt or an alkenyl succinate salt include a $C_8$ to $C_{22}$ hydrocarbon group, more specifically such as lauryl, myristyl, cetyl, stearyl and oleyl. Examples of the salt thereof include salts of sodium, potassium, lithium, ethanolamine, diethanolamine and triethanolamine.

[(A2) Sulfonate Type Anionic Surfactant]

A foaming agent is added to either or both of the first part and the second part so that stable foam is easily generated by mixing the liquid mixture in the two-part hair dye with air by a foam discharge means of the foamer vessel. As the foaming agent a sulfonate type anionic surfactant is added in order to generate the foam easy to apply and compatible to the hair.

Examples of the sulfonate type anionic surfactant include a sulfosuccinate type, an isethionate type, a taurinate type, an alkyl benzene sulfonic acid type, an α-olefin sulfonic acid type and an alkane sulfonic acid type.

Thereby, examples of the sulfosuccinate type anionic surfactant include a sulfosuccinate ester of a higher alcohol or an ethoxylate thereof, a sulfosuccinate ester derived from a higher fatty acid amide, and salts thereof as represented by the following general formula (3) or (4):

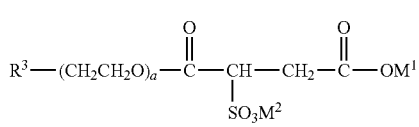
(3)

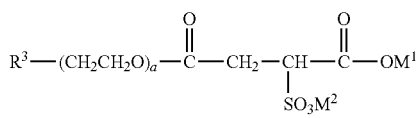
(4)

wherein $R^3$ represents $R^4$—O— or $R^5$—CO—NH— ($R^4$ represents a $C_8$ to $C_{22}$ linear or branched alkyl of alkenyl group, and $R^5$ represents a $C_7$ to $C_{21}$ linear or branched alkyl of alkenyl group), $M^1$ and $M^2$ represents a hydrogen atom or a cation forming a water-soluble salt selected from an alkali metal, alkaline earth metal, ammonium and organic ammonium, and "a" represents a number between 0 and 20.

Examples of the sulfosuccinate ester of the higher alcohol or the ethoxylate thereof among the compounds represented by the above general formula (3) or (4) include a disodium salt of a sulfosuccinate ester of a $C_{11}$ to $C_{13}$ secondary alcohol ethoxylate [SOFTANOL MES-3, 5, 7, 9, and 12 from Nippon Shokubai Co., Ltd. (wherein each number represents an average number of moles of the added ethylene oxide (EO))], a disodium salt of a sulfosuccinate ester of a lauryl alcohol or a lauryl alcohol ethoxylate (EO=3, 4, 6, 9 and 12; Kohacool L-400, etc. from Toho Chemical Industry Co., Ltd.), a disodium salt of a sulfosuccinate ester of a synthetic $C_{12}$ to $C_{15}$ primary alcohol or an ethoxylate thereof (EO=2 to 12), and a disodium salt of a sulfosuccinate ester of a C8 to C22 Guerbet alcohol or an ethoxylate thereof (EO=2 to 12). Examples of the sulfosuccinate ester derived from the higher fatty acid amide include a disodium salt of a sulfosuccinate ester of a polyethylene glycol (EO=1, 2) amide laurate, a disodium salt of sulfosuccinate of polyethylene glycol (EO=1, 2) amide oleate, and a disodium salt of a sulfosuccinate ester of a coconut oil fatty acid polyethylene glycol (EO=4) amide. Among others, in view of agreeable feel and foaming property, a sulfosuccinate ester or a salt thereof of a $C_{11}$ to $C_{13}$ linear higher alcohol or an ethoxylate thereof is preferable. Examples of $M^1$ and $M^2$ include sodium, potassium, ammonium, an alkanolamine and a basic amino acid. As the sulfosuccinate type anionic surfactant of the present invention, one or more compounds having different $R^3$, $M^1$ and $M^2$ moieties may be selected.

Examples of the isethionate type anionic surfactant include a compound represented by the following general formula (5):

(5)

wherein $R^6$ represents an alkyl, alkenyl or hydroxyalkyl group having an average carbon number of 7 to 19 and $M^3$ represents an alkali metal or an organic amine.

In the general formula (5), the fatty acid residue of $R^6COO$— include $C_{11}H_{23}COO$—, $C_{13}H_{27}COO$—, $C_{15}H_{31}COO$—, $C_{17}H_{35}COO$— and a coconut oil fatty acid residue, and the counter ion $M^3$ include lithium, potassium, sodium, ethanolamine, diethanolamine and triethanolamine.

Examples of the taurinate type anionic surfactant include a compound represented by the following general formula (6):

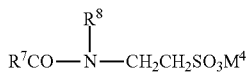
(6)

wherein $R^7$ represents an alkyl, alkenyl or hydroxyalkyl group having an average carbon number of 7 to 19, $R^8$ represents an lower alkyl or hydroxyalkyl group having an average carbon number of 1 to 3, and $M^4$ represents an alkali metal or an organic amine.

In the general formula (6), the acyl group of $R^7CO$— include lauroyl, palmitoyl, stearoyl, oleoyl, and a cocoyl group from a coconut oil fatty acid (the carbon atom numbers of $R^7$ of the acyl groups are distributed between 7 to 19). The alkyl group $R^8$ include methyl, ethyl and propyl, and the counter ion $M^4$ include lithium, potassium, sodium, triethanolamine, diethanolamine and ethanolamine.

Examples of the alkyl benzene sulfonic acid type anionic surfactant include a linear or branched alkyl benzene sulfonate salt having an alkyl group with an average carbon number of 10 to 16.

Examples of the α-olefin sulfonic acid type anionic surfactant include an α-olefin sulfonate salt having on average 10 to 20 carbon atoms in the molecule.

Examples of the alkane sulfonic acid type anionic surfactant include an alkane sulfonate salt having on average 10 to 20 carbon atoms in the molecule.

[(A3) Phosphate Type Anionic Surfactant]

A foaming agent is added to either or both of the first part and the second part so that stable foam is easily generated by mixing the liquid mixture in the two-part hair dye with air by a foam discharge means of the foamer vessel. As the foaming agent a phosphate type anionic surfactant is added in order to generate the foam easy to apply and compatible to the hair.

Examples of the phosphate type anionic surfactant include a compound represented by the following general formula (7) or (8):

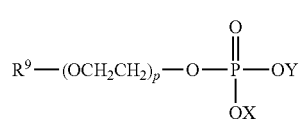
(7)

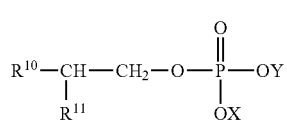
(8)

wherein $R^9$ represents a saturated or unsaturated $C_8$ to $C_{22}$ hydrocarbon group, $R^{10}$ represents a saturated or unsaturated $C_5$ to $C_{12}$ hydrocarbon group, $R^{11}$ represents a saturated or unsaturated $C_1$ to $C_4$ hydrocarbon group, X and Y represent respectively a hydrogen atom, an alkali metal, ammonium or an alkanolamine having a $C_2$ to $C_3$ hydroxyalkyl group, and "p" represents a number between 0 and 20.

In the general formula (7) $R^9$ is preferably a $C_8$ to $C_{22}$ alkyl or alkenyl group. The phosphate of the general formula (7) is preferably that with the addition mole number of ethylene oxide of 0 to 10, and more preferable is that with a $C_{12}$ to $C_{16}$ alkyl group without addition of ethylene oxide. For the phosphate according to the general formula (8), preferably $R^{10}$ is a $C_5$ to $C_{12}$ linear hydrocarbon group and $R^{11}$ is a $C_1$ to $C_4$ linear hydrocarbon group, and more preferably $R^{11}$ is a $C_8$ to $C_{12}$ linear hydrocarbon group and $R^{11}$ is a methyl group. Furthermore the compound, in which at least one of X and Y is potassium and the rest thereof is a hydrogen, is good in foaming.

The phosphate salt of the general formulas (7) and (8) is produced by reacting a corresponding aliphatic alcohol with a phosphorylation agent, such as phosphoric anhydride and phosphorus oxychloride, followed by neutralization with a base. Thereby as the aliphatic alcohol, a linear alcohol and a 2-branched alkyl alcohol may be used singly or premixed. A commercially available alcohol DIADOL 115L from Mitsubishi Chemical Corp. is a mixture of a linear alcohol and a 2-branched alkyl alcohol, and using the same a mixture of phosphate salts satisfying (8)/[(7)+(8)]=0.4 to 1 can be obtained.

The component (A3) also include a phosphate diester represented by the general formula (9):

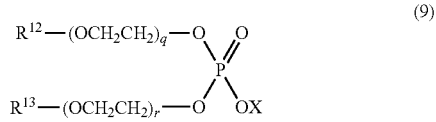

wherein $R^{12}$ and $R^{13}$ represent a saturated or unsaturated $C_8$ to $C_{18}$ hydrocarbon group, X represents a hydrogen atom, an alkali metal, ammonium or an alkanolamine having a $C_2$ to $C_3$ hydroxyalkyl group, and "q" and "r" represent respectively a number between 0 and 10.

Preferred specific examples of the component (A3) include sodium monolauryl phosphate, diethanolamine monolauryl phosphate, triethanolamine monolauryl phosphate, potassium monolauryl phosphate, sodium monomyristyl phosphate, potassium monomyristyl phosphate, diethanolamine monomyristyl phosphate, triethanolamine monomyristyl phosphate and a mixture of phosphate salts obtained by a reaction between an alcohol mixture such as the DIADOL 115L and the phosphorylation agent.

Two or more of the anionic surfactants selected from the components (A1) to (A3) may be used together, and added in either or both of the first part and the second part. The content in the liquid mixture of the first and second parts is preferably 0.01 to 20% by mass, more preferably 0.1 to 10% by mass, and even more preferably 0.5 to 7% by mass so that the foam easily applicable and compatible to the hair can be formed. If it is added to the first part, the content therein is preferably 0.01 to 30% by mass to discharge the good quality foam stably over time, more preferably 0.1 to 20% by mass and even more preferably 0.3 to 10% by mass. If it is added to the second part, the content therein is preferably 0.01 to 30% by mass to discharge the good quality foam stably over time, more preferably 0.1 to 20% by mass and even more preferably 0.3 to 10% by mass.

[Other Surfactants than (A1) to (A3)]

To the two-part hair dye using an anionic surfactant selected from the components (A1) to (A3) of the present invention may include additionally other surfactants so that the foam further easily applicable and compatible to the hair can be formed. Examples of such surfactants include an anionic surfactant other than the components (A1) to (A3), an amphoteric surfactant, a semipolar surfactant, a nonionic surfactant and a cationic surfactant.

Examples of an anionic surfactant other than the components (A1) to (A3) include an alkyl sulfate ester type anionic surfactant, such as an alkyl sulfate and an alkyl ether sulfate.

Examples of the amphoteric surfactant include amphoteric surfactants of a carbobetaine type, an amidobetaine type, a sulfobetaine type, a hydroxyl sulfobetaine type, an amidosulfobetaine type, a phospho-betaine type, and an imidazolinium type, having a $C_8$ to $C_{24}$ alkyl, alkenyl or acyl group.

Examples of the semipolar surfactant include an alkyl amine oxide.

Examples of the nonionic surfactant include nonionic surfactants of a polyoxyethylene alkyl ether type, a polyoxyethylene fatty acid ester type, an alkyl glyceryl ether type, a glycerin fatty acid ester type, a fatty acid alkanolamide type, a sugar ether type, a sugar ester type and a sugar amide type.

Examples of the cationic surfactant include cationic surfactants of a tertiary amine salt type and a quaternary ammonium salt type, having a $C_8$ to $C_{24}$ alkyl, alkenyl or acyl group.

Two or more of the surfactants other than the components (A1) to (A3) may be used together, and added in either or both of the first part and the second part. The content in the liquid mixture of the first and second parts is preferably 0.01 to 10% by mass, more preferably 0.1 to 7% by mass, and even more preferably 0.2 to 5% by mass so that the foam easily applicable and compatible to the hair can be formed.

<(A4) Ionic Surfactant+(A5) Fatty Acid Alkanolamide>

Meanwhile, if a combination of the (A4) ionic surfactant and (A5) fatty acid alkanolamide is used as the surfactant, the two-part hair dye in the form of foam, which is superior in a foaming property at a lower temperature and resistant to drip from the application of the liquid mixture to the hair until being washed away, can be obtained.

[(A4) Ionic Surfactant]

The ionic surfactant is added to either or both of the first part and the second part so that stable foam is easily generated by mixing the liquid mixture in the two-part hair dye with air by a foam discharge means of the foamer vessel. Examples of the ionic surfactant include an anionic surfactant, a cationic surfactant and an amphoteric surfactant and the anionic surfactant, the cationic surfactant and the amphoteric surfactant are preferred, with the anionic surfactant being more preferred so that foaming favorable to easy application to the hair can be attained, even when the liquid is at a lower temperature or near ordinary temperature.

Examples of the anionic surfactant include a sulfate ester surfactant, such as an alkyl sulfate and an alkyl ether sulfate; a carboxylate surfactant, such as a fatty acid salt, an N-acylamino acid salt (e.g. N-acylsarcosine salt, N-acylglutamic acid salt and N-acylglycin salt), a salt of an alkylsuccinate or alkenylsuccinate, an alkyl ether carboxylic acid salt, and a fatty acid amide ether acetic acid salt; a phosphate surfactant, such as an alkyl phosphate salt, and an alkyl ether phosphate salt; a sulfonate surfactant, such as a sulfosuccinic acid salt, an isethionic acid salt, a taurine salt, an alkylbenzene sulfonic acid, an α-olefin sulfonic acid, and an alkane sulfonic acid. Preferred are an alkyl sulfate and a polyoxyalkylene alkyl sulfate, and more preferred are the same with the alkyl group having $C_{10}$ to $C_{24}$, further preferred $C_{12}$ to $C_{18}$, and the alkyl group is preferably linear. Further, the polyoxyalkylene alkyl sulfate is more preferable, and a polyoxyethylene alkyl sulfate is even more preferable, among others those with the average addition mole number of the oxyethylene group of 1 to 10 are preferred, with those of 2 to 5 being more preferred. Also preferred are an N-acylamino acid salt and an ether carboxylic acid salt, and N-acylglutamic acid salt, whose acyl group has $C_{10}$ to $C_{18}$, and a polyoxyethylene alkyl carboxylic acid salt, whose alkyl group has $C_{10}$ to $C_{18}$, and which has the average addition mole number of the oxyethylene group of 3 to 15, are preferable.

Examples of the cationic surfactant can include a compound represented by the following general formula (10):

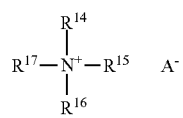

$$R^{17}-\underset{\underset{R^{16}}{|}}{\overset{\overset{R^{14}}{|}}{N^+}}-R^{15} \quad A^- \tag{10}$$

wherein $R^{14}$, $R^{15}$, $R^{16}$ and $R^{17}$ represent independently a hydrocarbon group, which may be substituted, at least one of $R^{14}$ and $R^{15}$ has $C_8$ to $C_{36}$, and the rest has $C_1$ to $C_7$, or $R^{16}$ and $R^{17}$ together with the adjacent nitrogen atom may form a 5- to 7-membered ring, which may contain in addition to the nitrogen atom, a nitrogen atom, an oxygen atom and a sulfur atom as hetero-atoms, and may be substituted with a $C_1$ to $C_4$ alkyl group. "$A^-$" represents an anion.

Examples of the hydrocarbon group include a linear or branched-chain alkyl group, a linear or branched-chain alkenyl group, an aryl group and an aralkyl group, and examples of the substituent include a hydroxy group, an alkoxy group, an aryloxy group, an epoxy group, an amino group, a mono- or di-alkylamino group, a trialkylammonium group, a fatty acid amide group, and a fatty acid ester group. Examples of the ring which $R^{16}$ and $R^{17}$ together with the adjacent nitrogen atom form, include a morpholine ring, an imidazoline ring, a piperazine ring, a piperidine ring, and a pyrrolidine ring.

Examples of the anion include a chloride ion, a bromide ion, an iodide ion, a methylsulfate ion, an ethylsulfate ion, an acetate ion, a phosphate ion, a sulfate ion, a lactate ion, and a saccharin ion.

Specific examples of the cationic surfactant include cetyltrimethylammonium chloride, stearyltrimethylammonium chloride, isostearyltrimethylammonium chloride, lauryltrimethylammonium chloride, behenyltrimethylammonium chloride, octadecyltrimethylammonium chloride, cocoyltrimethylammonium chloride, cetyltrimethylammonium bromide, stearyltrimethylammonium bromide, lauryltrimethylammonium bromide, isostearyllauryldimethylammonium chloride, dicetyldimethylammonium chloride, distearyldimethylammonium chloride, dicocoyldimethylammonium chloride, γ-gluconamidopropyldimethylhydroxyethylammonium chloride, di[polyoxyethylene(2)]oleylmethylammonium chloride, dodecyldimethylethylammonium chloride, octyldihydroxyethylmethylammonium chloride, tri[polyoxyethylene(5)]stearylammonium chloride, polyoxypropylenemethyldiethylammonium chloride, lauryldimethyl(ethylbenzyl)ammonium chloride, behenamidopropyl-N,N-dimethyl-N-(2,3-dihydroxypropyl)ammonium chloride, tallowedimethylammoniopropyltrimethylammonium dichloride, and benzalkonium chloride.

As the cationic surfactant, a monoalkyltrimethylammonium salt and dialkyldimethylammonium salt, namely the compounds in which one or both of $R^{14}$ and $R^{15}$ is a linear or branched-chain $C_8$ to $C_{30}$, or preferably $C_{10}$ to $C_{24}$, especially $C_{12}$ to $C_{18}$ alkyl group, and the rest is a methyl group, are preferable, and a monoalkyltrimethylammonium salt is more preferable.

Examples of the amphoteric surfactant include surfactants of a carbobetaine type, an amidobetaine type, a sulfobetaine type, a hydroxysulfobetaine type, an amidosulfobetaine type, a phosphobetaine type and an imidazolinium type, having a $C_8$ to $C_{24}$ alkyl, alkenyl or acyl group, and among others the carbobetaine type surfactant and the sulfobetaine type surfactant are preferable. Specific examples of the preferable amphoteric surfactant include lauramidopropyl betaine, coconut oil fatty acid amidopropyl betaine, lauryldimethylaminoacetic acid betaine and laurylhydroxysulfobetaine.

Two or more of the ionic surfactants of the component (A4) may be used together, and the content in the liquid mixture of the first and second parts is preferably 0.1 to 30% by mass, more preferably 1 to 20% by mass, and even more preferably 2 to 10% by mass.

[(A5) Fatty Acid Alkanolamide]

The fatty acid alkanolamide of the component (A5) is used in order to improve the foam stability so that the two-part hair dye of the present invention should be prevented from dripping after application to the hair while being left thereon.

A preferable fatty acid alkanolamide has a $C_8$ to $C_{22}$, preferably $C_{10}$ to $C_{16}$ acyl group. As the fatty acid alkanolamide either of a monoalkanolamide and a dialkanolamide is usable, and those having a $C_2$ to $C_3$ hydroxyalkyl group are preferable. Examples of such preferable fatty acid alkanolamide include oleamide DEA, palm kernel oil fatty acid diethanolamide, cocamide DEA, lauramide DEA, polyoxyethylene coconut oil fatty acid monoethanolamide, coconut oil fatty acid monoethanolamide, lauric acid isopropanolamide, and lauric acid monoethanolamide. Among them a fatty acid diethanolamide is preferred.

Two or more of the fatty acid alkanolamides may be used together, and added in either or both of the first part and the second part. The content in the liquid mixture of the first and second parts is preferably 0.1 to 15% by mass, more preferably 0.3 to 10% by mass, and even more preferably 0.5 to 5% by mass in view of foamability, obtaining fine and soft foam quality, and preventing dripping during being left on the hair.

[Other Surfactants than Components (A4) and (A5)]

To the two-part hair dye using the components (A4) and (A5) of the present invention, surfactants other than fatty acid alkanolamide, such as a nonionic surfactant and a semipolar surfactant, may further be contained. Two or more of such other surfactants may be used together.

Examples of the nonionic surfactant include an alkyl polyglucoside, a polyoxyalkylene alkyl ether, an alkyl glyceryl ether. For the alkyl polyglucoside, the carbon number of the alkyl group is preferably 8 to 18, more preferably 8 to 14, and even more preferably 9 to 11, and the alkyl group is preferably linear. The average degree of polymerization of the glucoside is preferably 1 to 5, more preferably 1 to 2. For the polyoxyalkylene alkyl ether the carbon number of the alkyl group is preferably 10 to 22, more preferably 12 to 18, and the alkyl group is preferably linear. A polyoxyethylene alkyl ether is more preferable, with that having an average addition mole number of the oxyethylene group of 1 to 40 being more preferable, and that of 4 to 30 being even more preferable. For the alkyl glyceryl ether, the carbon number of the alkyl group is preferably 8 to 18, more preferably 8 to 12, and the alkyl group is preferably a branched-chain.

Examples of the semipolar surfactant include an alkylamine oxide.

<Higher Alcohol>

The two-part hair dye of the present invention may contain additionally a higher alcohol in order to improve the foam stability so that the two-part hair dye of the present invention should not drip after application to the hair during being left thereon.

The higher alcohol has preferably a $C_{10}$ to $C_{30}$, more preferably $C_{12}$ to $C_{24}$, even more preferably $C_{14}$ to $C_{22}$ alkyl or alkenyl group, more preferably the alkyl group, and even more preferably the linear alkyl group. Examples thereof include myristyl alcohol, cetanol, stearyl alcohol, arachyl alcohol, behenyl alcohol, and oleyl alcohol.

Two or more of the higher alcohols may be used together, and added in either or both of the first part and the second part. The content of the higher alcohol in the liquid mixture of the first and second parts is preferably 0.01 to 1% by mass, more preferably 0.1 to 0.8% by mass, even more preferably 0.2 to 0.7% by mass and even more preferably 0.3 to 0.6% by mass, in view of foamability, obtaining fine and soft foam quality, and preventing dripping during being left on the hair. In case the higher alcohol is added to the first part, the content therein is preferably 0.01 to 2% by mass, more preferably 0.1 to 1.5% by mass, and even more preferably 0.2 to 1% by mass. In case the higher alcohol is added to the second part, the content therein is preferably 0.01 to 2% by mass, more preferably 0.1 to 1.5% by mass and even more preferably 0.5 to 1% by mass.

If the two-part hair dye of the present invention uses the combination of (A4) the ionic surfactant and (A5) the fatty acid alkanolamide, in view of the foaming property at a lower temperature, the higher alcohol should be preferably not contained or contained in a small amount. From this view point, the content of the higher alcohol in the liquid mixture of the first and second parts of such a two-part hair dye is preferably 0 to 0.8% by mass, more preferably 0.01 to 0.7% by mass, and even more preferably 0.1 to 0.6% by mass.

<Nonvolatile Hydrophilic Solvent>

Preferably either of the first part and the second part contains also a nonvolatile hydrophilic solvent. Owing thereto, the irritation to the scalp caused by the concentration of irritating components such as hydrogen peroxide due to the evaporation of water from the hair dye, while the applied two-part hair dye of the present invention is left on the hair, can be reduced. As the nonvolatile hydrophilic solvent, polyols and lower alkyl ($C_1$ to $C_4$) ethers thereof not having antifoaming activity are preferable. For polyols, those with $C_2$ to $C_6$ are preferable. Examples thereof include glycerin, diglycerin, propylene glycol, dipropylene glycol, 1,3-butanediol, ethylene glycol, diethylene glycol, isoprene glycol, and sorbitol. Examples of the lower alkyl ethers of the polyols include a mono-lower alkyl ether and a poly-lower alkyl ether (e.g. di-lower alkyl ether) of the polyol. Among others, a monomethyl ether or a monoethyl ether of the polyol is preferable. Specific examples thereof include ethylene glycol monomethyl ether, ethylene glycol monoethyl ether, diethylene glycol monomethyl ether and diethylene glycol monoethyl ether. Two or more thereof may be used together.

The content of the nonvolatile hydrophilic solvent in the liquid mixture of the first and second parts is preferably 0.01 to 4% by mass, more preferably 0.1 to 3% by mass, and even more preferably 0.2 to 2% by mass in order to decrease the irritation to the scalp and to obtain the quality foam at a lower temperature.

<Dye>

The two-part hair dye of the present invention can be used for bleaching the hair, when the liquid mixture of the first and second parts does not contain a dye, and used for dyeing the hair, when the liquid mixture contains an oxidation dye or a direct dye. For dying purpose, the first part contains the oxidation dye or the direct dye. Examples of the oxidation dye include a dye precursor, such as p-phenylenediamine, p-aminophenol, toluene-2,5-diamine, N,N-bis(2-hydroxyethyl)-p-phenylenediamine, 2-(2-hydroxyethyl)-p-phenylenediamine, 4-amino-3-methylphenol, 6-amino-3-methylphenol, o-aminophenol, and 1-hydroxyethyl-4,5-diaminopyrazole; and a coupler, such as resorcinol, 2-methylresorcinol, m-aminophenol, p-amino-o-cresol, 5-(2-hydroxyethylamino)-2-methylphenol, m-phenylenediamine, 2,4-diaminophenoxyethanol, and 1-naphthol. Examples of the direct dye include p-nitro-o-phenylenediamine, p-nitro-m-phenylenediamine, Basic Yellow 87, Basic Orange 31, Basic Red 12, Basic Red 51, Basic Blue 99.

<Silicones>

In order to keep the discharged foam stable for a long time, it is desirable that the two-part hair dye of the present invention does not contain a silicone in the liquid mixture of the first and second parts. However, to make the foam smooth and compatible to the hair and to impart a high conditioning effect to the hair, the liquid mixture may contain also a silicone within a certain range. Examples of the silicones include dimethylpolysiloxane, methylphenylpolysiloxane, polyether modified silicone, amino modified silicone, oxazoline modified silicone elastomer and emulsions dispersing the same in water using a surfactant. Among them, polyether modified silicone, amino modified silicone, and the emulsions thereof are preferable, because they can be dispersed in water stably without using a thickener.

Polyether modified silicone includes an end-modified type and a side chain-modified type, such as a pendant (pectinate) type, a both end-modified type, a one end-modified type. Examples of the modified silicone include a dimethylsiloxane/methyl(polyoxyethylene)siloxane copolymer, a dimethylsiloxane/methyl(polyoxypropylene)siloxane copolymer, and a dimethylsiloxane/methyl(polyoxyethylene-polyoxypropylene)siloxane copolymer. The HLB of the polyether modified silicone is preferably 10 or higher, more preferably 10 to 18, in view of compatibility with water. Thereby the HLB values are to be determined by the phenol index (the phenol index is an index correlated with HLB, applicable to an ether type nonionic surfactant).

Although the amino modified silicone having an amino group or an ammonium group is usable, amodimethicone is preferred.

If the silicone is added in the liquid mixture of the first and second parts, the content thereof is preferably 2% by mass or less, more preferably 0.005 to 1% by mass, and even more preferably 0.01 to 0.5% by mass in order not to interfere with foaming, and to make the foam smooth and compatible to the hair, and to impart a high conditioning effect to the hair.

<Other Components>

The first part and the second part may contain as necessary a perfume, a UV absorber, a metal chelating agent such as edetic acid, an antibacterial agent, an antiseptic agent such as methyl-p-hydroxybenzoate, a stabilizer, such as phenacetin, etidronic acid, or oxyquinoline sulfate, an organic solvent, such as ethanol, benzyl alcohol, or benzyloxy ethanol, a water-soluble polymer such as hydroxyethyl cellulose, and a humectant. The liquid mixture of the first and second parts contains preferably a medium composed mainly of water.

Further, a persulfate such as ammonium persulfate may be added in the liquid mixture as the third part in order to improve the bleaching activity.

<Viscosity>

The viscosity (25° C.) of the first part is preferably 1 to 50 mPa·s, more preferably 3 to 40 mPa·s, and even more preferably 5 to 30 mPa·s. The viscosity (25° C.) of the second part is preferably 1 to 300 mPa·s, more preferably 3 to 200 mPa·s, and even more preferably 5 to 100 mPa·s. The viscosity (25°

C.) of the liquid mixture of the first and second parts is preferably 1 to 300 mPa·s, more preferably 1 to 100 mPa·s, even more preferably 3 to 100 mPa·s, even more preferably 3 to 80 mPa·s, even more preferably 3 to 50 mPa·s, even more preferably 5 to 50 mPa·s, even more preferably 5 to 30 mPa·s, and even more preferably 10 to 30 mPa·s. The viscosity is measured by a B-type rotational viscometer (Model TV-10 from Tokimec Inc.) using a rotor No. 1 which is rotated for 1 min. before the measurement. If the viscosities of subjects to be measured are 100 mPa·s or below, between 100 and 200 mPa·s or between 200 and 500 mPa·s, the measurement is conducted at the rotation speeds of 60 rpm, 30 rpm, and 12 rpm, respectively. By adjusting the viscosity of the liquid mixture in the above range, the liquid mixture can be mixed uniformly without foaming, which can form uniform foams easily applicable to the hair, compatible to the hair, and resistant to drip after the application.

By adjusting the viscosity in the above range, the foam easily applicable and compatible to the hair and resistant to drip after the application to the hair can be obtained, and discharge of the foam from the non-aerosol foamer vessel becomes easy. For adjusting the viscosity within such range, a water-soluble solvent such as ethanol is added, or the contents and types of a surfactant, a polyol, or a higher alcohol should be appropriately adjusted.

<Air/Liquid Mixing Ratio>

The air/liquid mixing ratio (air/the liquid mixture) of the foam discharged from the foamer vessel is preferably 10 to 50 mL/g, more preferably 15 to 40 mL/g, and even more preferably 20 to 30 mL/g in view of compatibility and easy applicability of the foam to the hair. Thereby the air/liquid mixing ratio is measured as follows.

The air/liquid mixing ratio is determined by measuring the mass and the volume of the foam discharged at 25° C. In the foamer vessel 100 g of the liquid mixture is poured and 20 g of foam is discharged into a 1,000 mL-measuring cylinder and the volume thereof is measured 1 min. after the start of discharging. The discharged foam volume (mL) is divided by the mass of 20 g to give the air/liquid mixing ratio (mL/g).

<Foamer Vessel>

The foamer vessel of the present invention is a non-aerosol vessel that discharges in the form of foam the two-part hair dye by mixing it with air without using a propellant. Moreover, with the use of the foamer vessel, spattering of the discharged dye can be prevented. A non-aerosol vessel can be produced at a lower cost compared with an aerosol vessel, can be regulated easily for the discharging speed, is recyclable with certain treatment, and can be handled safely during the product distribution because a high pressure propellant gas is not involved.

As the foamer vessel, any non-aerosol vessel with a foam discharging means, such as a pump foamer vessel and a squeeze foamer vessel publicly known and having a foam discharging means, can be used.

The pump foamer or squeeze foamer vessel has a foam generating part such as a net, whose thickness is preferably thin so that clogging caused by the dried-up liquid mixture of the first and second parts can be immediately removed at the next discharge by the foam flow dissolving the clogged sold. Thereby the mesh size of the net is preferably 50 to 280 mesh, more preferably 90 to 250 mesh, and even more preferably 130 to 220 mesh. By use of the net with such mesh size, creamy foam can be generated. Preferable examples of a material for the net include nylon, polyethylene, polypropylene, polyester, Teflon (registered trade name), carbon fibers, and stainless steel. More preferable are nylon, polyethylene, polypropylene, and polyester, and even more preferable is nylon.

The foamer vessel to be used for the two-part hair dye of the present invention is provided with at least one of such net, preferably a plurality of the same, and more preferably 2 of the same in view of economy and stability of the foam. Thereby the mesh size of the net that the liquid first passes is coarser than or same as the net passed next.

A part of the foamer vessel that contacts the content (e.g. the inner wall of the vessel, the inner wall of the foaming discharging means) is preferably composed of a material that is not corroded by alkali or hydrogen peroxide, and is permeable to oxygen generated by decomposition of the hydrogen peroxide.

As a product form of the two-part hair dye of the present invention composed of the first part, the second part and the foamer vessel, the first part and the second part may be filled in respective vessels separated from the foamer vessel and they are transferred to the foamer vessel before use to be mixed, or either part may be filled in the foamer vessel, while the other part is packaged in a separate vessel, which is transferred to the foamer vessel before use. Thereby the second part is preferably filled in the foamer vessel constituted of a vessel with gas permeability so that the increase of the vessel inner pressure by the oxygen generated by the decomposition of the hydrogen peroxide can be prevented, more preferably filled in the foamer vessel constituted with a material having oxygen permeability (e.g. polypropylene and polyethylene). In contrast, for the first part an oxygen non-permeable vessel should be used to prevent oxidation of the oxidation dye.

<Method for Dyeing Hair>

In the method for dyeing the hair according to the present invention, the hair should preferably be combed in advance of application of the discharged foam, which suppresses the hair to tangle during a refoaming treatment and prevents the hair dye from spattering. Further, after combing the hair, the blocking procedure as commonly conducted is not required, and the omission of the blocking procedure is preferable. This makes the step of applying the hair dye to the hair and the step of refoaming described below easier.

The hair to be treated by the hair dye should preferably have not been treated with a hair dressing immediately before the dyeing treatment, so that dripping is prevented, uniform dyeing and a sufficient dyeing effect can be obtained. Further the hair should be preferably dry so that the liquid mixture is not diluted, dripping is prevented, and uniform dyeing and a sufficient dyeing effect can be obtained. If the hair is shampooed immediately before the hair dyeing treatment, the hair should be preferably dried before the dyeing treatment. Thereby drying the hair means to remove a liquid composed mainly of water attached to the hair by reason of the shampooing, to the extent that the liquid does not spontaneously drip. Specifically, towel-drying or blow-drying is preferable.

The liquid mixture of the first and second parts discharged in the form of foam is, after once receiving the same by hand or a brush, or directly, applied to the hair. If it is received by hand, it is preferable to wear gloves. Since by the method for dyeing the hair according to the present invention, the blocking procedure as commonly conducted in applying the hair dye can be omitted, the foam can be applied quickly. Consequently, application can start at an arbitrary location of the hair, differently from the rule for a conventional liquid or creamy two-part hair dye, that the application need not start from the hair at the neckline. The application may start at a location of interest, and preferably start at the hairline or the part.

It is preferable to discharge the foam approximately to a lemon size, because the size is appropriate to receive by one hand and to apply the same to the hair by the hand. In this case, the procedure to discharge the foam is conducted by a hand, which is received by the other hand. After the once received foam is applied to the hair, the procedures of the discharge of the foam to the hand and the application thereof to the hair are repeated. This series of the procedures can be carried out very easily and quickly.

The applied range of the foam may be the entirety of the hair or only a specific part thereof.

Next, the applied foam is foamed up again on the hair. This refoaming may be conducted by gas injection, by use of an instrument, such as a vibrator or a brush, or by fingers, however use of fingers is preferable, because thereby the two-part hair dye can be spread also to the hair root adequately. The refoaming speed with the vibrator, the brush or the fingers should be preferably so regulated, that the foam does not splash around.

Thereby the refoaming may be conducted after the foam has completely disappeared, or during the foam is disappearing, or before the applied foam starts to change. Further, it may be conducted after the foam is applied to all the intended area, or halfway in the application. The refoaming may be conducted once continuously, or intermittently repeated more than once. Thereby continuous refoaming means the vibrator, the brush or the fingers used for refoaming continue to touch a part of the hair, or retouch the same within 1 sec., even if the contact is lost once. In short, observing the applied region, the foam should be refoamed appropriately at latest before the dripping of a liquid from the applied foam should take place. By refoaming the disappearing foam, the dripping can be prevented irrespective of the nature of the foam. Furthermore, despite of a difference in the nature of a foam caused by a difference in a structure of the foamer vessel or the composition of the two-part hair dye, the nature of the foam can be modified to that suitable for hair dyeing by the refoaming. Although it may be possible to obtain the foam maintaining stably the quality suitable for hair dyeing without dripping by selecting specifically a structure of the foamer vessel and the composition of the two-part hair dye, it is still desirable in such a case to refoam at least once as soon as possible after the completion of the application of the form. The refoaming at an earlier stage can prevent unevenness in color over the region to be applied. The timing thereof is preferably within 5 min. after the completion of the application of the discharged foam to the hair, more preferably within 3 min., and even more preferably within 1 min.

Specific examples of the preferable stepwise procedure of discharging the foam, applying the same to the hair, and refoaming will be described separately for partial dyeing and whole head dyeing.

[Partial Dyeing]

1) An appropriate amount of the foam is discharged onto a hand, which is applied to a part of the hair and refoamed once for 1 sec. to 10 preferably for 3 sec. to 3 min.

2) An appropriate amount of the foam is discharged onto a hand, which is applied to a part of the hair and refoamed 2 to 30 times, each time for 1 sec. to 10 min., preferably for 3 sec. to 3 min., totally spending 2 sec. to 20 min., and preferably 5 sec. to 5 min.

[Whole Head Dyeing]

3) An appropriate amount of the foam is discharged onto a hand, which is applied to a part of the hair and refoamed once for 3 sec. to 10 min., preferably for 5 sec. to 3 min. The procedure is repeated to apply the foam to the whole head.

4) An appropriate amount of the foam is discharged onto a hand, which is applied to a part of the hair and refoamed once for 3 sec. to 10 min., preferably for 5 sec. to 3 min. The procedure is repeated to apply the foam to the whole head, and then refoamed once for 3 sec. to 10 min., preferably for 5 sec. to 3 min. Further, an appropriate amount of the foam is discharged onto a hand, which is applied to a part of the hair additionally and refoamed over the whole head once for 3 sec. to 10 min., preferably for 5 sec. to 3 min.

5) An appropriate amount of the foam is discharged onto a hand, which is applied to a part of the hair and refoamed once for 3 sec. to 10 min., preferably for 5 sec. to 3 min. The procedure is repeated to apply the foam to the whole head. After the completion of the application to the whole head, the refoaming is conducted once for 3 sec. to 10 min., preferably 5 sec. to 5 min.

6) An appropriate amount of the foam is discharged onto a hand, which is applied to a part of the hair and refoamed once for 3 sec. to 10 min., preferably for 5 sec. to 3 min. The procedure is repeated to apply the foam to the whole head. After the completion of the application to the whole head, the refoaming over the whole head is conducted 2 to 30 times each time for 3 sec. to 10 min., preferably 5 sec. to 3 min., totally spending 6 sec. to 20 min., preferably 10 sec. to 5 min.

7) An appropriate amount of the foam is discharged onto a brush, which is applied to a part of the hair. The procedure is repeated to apply the foam to the whole head and refoamed with the same brush over the whole head for 3 sec. to 10 min., preferably for 5 sec. to 5 min.

8) An appropriate amount of the foam is discharged onto a brush, which is applied to a part of the hair and refoamed once with the same brush or by hand over 3 sec. to 10 min., preferably for 5 sec. to 3 min. The procedure is repeated to apply the foam to the whole head. After the completion of the application to the whole head, the refoaming is conducted once with the same brush or by hand for 3 sec. to 10 min., preferably 5 sec. to 5 min.

The refoaming may be conducted over the whole hair or over a limited region. If the refoaming is conducted over the whole hair, even when the foam be failed to be applied to an unseeable part such as the hair at the back of the head, the foam can be distributed totally and an undyed area can be eliminated. If the refoaming is carried out at a certain limited area by a partial dyeing, the border of the dyed area can be gradated to give a natural finish. Furthermore, after refoaming the distribution of the foam becomes easily seeable, and existence of an undyed part in the area to be dyed can be avoided.

The foam is washed off about 3 to 60 min., preferably about 5 to 45 min. after the completion of the application thereof. Thereby the time after the completion of the application of the form is the total required time from the completion of the application of the foam to the whole head or the intended area, until the washing, namely a concept including the time for being left on the hair as well as the time required for refoaming. Thereafter the hair is appropriately shampooed, rinsed, washed with water and dried.

EXAMPLES

Examples 1 to 12 and Comparative Example 1

The first part and the second part of each two-part hair dye according to the compositions listed in Tables 1 to 3 were prepared, and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed.

Comparative evaluations between the two-part hair dyes in the form of foam of Examples 1 to 12, and Comparative Example 1 on "applicability of the foam" and "compatibility of the foam" were carried out by 10 test subjects as follows: To the wig of the same hairstyle with the hair cut on the chin line (Beaulax Co., Ltd., No. 775S), the subjects were asked to carry out the following application procedure starting from the dry state of the hair, with the respective two-part hair dyes in the form of foam.

1. To the vessel of the squeeze foamer containing 60 g of the second part, 40 g of the first part was added, and the liquid mixture of the first and second parts is mixed avoiding foaming and the squeeze foamer is mounted.
2. After wearing gloves, the squeeze vessel standing upright is squeezed by one hand to discharge the liquid mixture in the form of foam onto the palm of the other hand.
3. The liquid mixture in the form of foam is applied to the dry hair.
4. Repeating the steps 2 and 3, 80 g of the liquid mixture is applied to the whole hair.
5. The applied liquid mixture is refoamed by massaging the whole hair with fingers for 15 sec.
6. Leave it for 10 min.
7. The applied liquid mixture is refoamed by massaging the whole hair with fingers for 25 sec.
8. After the completion of the refoaming according to the step 7, leave it for 20 min.
9. The whole hair is washed with warm water, followed by shampooing, rinsing and drying successively.

The rating points are defined as below relative to Comparative Example 1 as the bench mark (containing Na laureth sulfate as an anionic surfactant, as in the example of Patent Document 1), and the sums of the rated points are shown also in Tables 1 to 3.

[Rating Points]
"Applicability of Foam"
Substantially better applicability than Comparative Example 1:
+2 point
Better applicability than Comparative Example 1:
+1 point
Equivalent applicability to Comparative Example 1:
0 point
Poorer applicability than Comparative Example 1:
−1 point
Substantially poorer applicability than Comparative Example 1:
−2 point
"Compatibility of Foam"
Substantially better compatibility than Comparative Example 1:
+2 point
Better compatibility than Comparative Example 1:
+1 point
Equivalent compatibility to Comparative Example 1:
0 point
Poorer compatibility than Comparative Example 1:
−1 point
Substantially poorer compatibility than Comparative Example 1:
−2 point Furthermore, each mixture of the first part and the second part at the ratio by mass of 1:1.5 was applied to each goat hair tress (10 cm, about 1 g, from Beaulax Co., Ltd.) at the bath ratio of 1:1, left thereon for 30 min., and then washed with water and shampooed. After drying, the color of the tress was measured by a colorimeter (CR400 from Konica Minolta Sensing Inc.) and the "dyeability" was evaluated by the color difference ($\Delta E$) from that of the goat hair tress before dyeing. The average value of the evaluation results (N=3) was used for comparison.

TABLE 1

|  | Ex. | | | | | Com. Ex. |
| --- | --- | --- | --- | --- | --- | --- |
|  | 1 | 2 | 3 | 4 | 5 | 1 |
| First part (% by mass) | | | | | | |
| p-Aminophenol | 0.3 | 0.3 | 0.3 | 0.3 | 0.3 | 0.3 |
| m-Aminophenol | 0.1 | 0.1 | 0.1 | 0.1 | 0.1 | 0.1 |
| p-Amino-o-cresol | 0.3 | 0.3 | 0.3 | 0.3 | 0.3 | 0.3 |
| Toluene-2,5-diamine | 0.9 | 0.9 | 0.9 | 0.9 | 0.9 | 0.9 |
| Resorcinol | 0.8 | 0.8 | 0.8 | 0.8 | 0.8 | 0.8 |
| Aqueous ammonia (28% by mass) | 3.0 | 3.0 | 3.0 | 3.0 | 3.0 | 3.0 |
| Ethanolamine | 1.0 | 1.0 | 1.0 | 1.0 | 1.0 | 1.0 |
| Ammonium hydrogencarbonate | 2.5 | 2.5 | 2.5 | 2.5 | 2.5 | 2.5 |
| Sodium cocoyl glutamate | 5.0 | — | — | — | — | — |
| Sodium lauroyl sarcosine | — | 5.0 | — | — | — | — |
| Sodium laureth-11 acetate | — | — | 5.0 | — | — | — |
| Sodium laureth-6 acetate | — | — | — | 5.0 | — | — |
| TEA laurate | — | — | — | — | 5.0 | — |
| Sodium laureth sulfate | — | — | — | — | — | 5.0 |
| Ethanol | 10.0 | 10.0 | 10.0 | 10.0 | 10.0 | 10.0 |
| Propylene glycol | 4.0 | 4.0 | 4.0 | 4.0 | 4.0 | 4.0 |
| EDTA-4Na | 0.1 | 0.1 | 0.1 | 0.1 | 0.1 | 0.1 |
| Ascorbic acid | 0.4 | 0.4 | 0.4 | 0.4 | 0.4 | 0.4 |

TABLE 1-continued

|  | Ex. 1 | Ex. 2 | Ex. 3 | Ex. 4 | Ex. 5 | Com. Ex. 1 |
|---|---|---|---|---|---|---|
| Anhydrous sodium sulfite | 0.5 | 0.5 | 0.5 | 0.5 | 0.5 | 0.5 |
| Perfume | 0.5 | 0.5 | 0.5 | 0.5 | 0.5 | 0.5 |
| Water | Balance | Balance | Balance | Balance | Balance | Balance |
| Second part (% by mass) | | | | | | |
| Aqueous hydrogen peroxide solution (35% by mass) | 16.3 | 16.3 | 16.3 | 16.3 | 16.3 | 16.3 |
| Sodium cocoyl glutamate | 5.0 | — | — | — | — | — |
| Sodium lauroyl sarcosine | — | 5.0 | — | — | — | — |
| Sodium laureth-11 acetate | — | — | 5.0 | — | — | — |
| Sodium laureth-6 acetate | — | — | — | 5.0 | — | — |
| TEA laurate | — | — | — | — | 5.0 | — |
| Sodium laureth sulfate | — | — | — | — | — | 5.0 |
| Cetanol | 0.6 | 0.6 | 0.6 | 0.6 | 0.6 | 0.6 |
| Etidronic acid | 0.08 | 0.08 | 0.08 | 0.08 | 0.08 | 0.08 |
| Aqueous sodium hydroxide solution (48% by mass) | * | * | * | * | * | * |
| Water | Balance | Balance | Balance | Balance | Balance | Balance |
| Applicability of foam | +10 | +10 | +9 | +8 | +10 | Bench mark |
| Compatibility of foam | +10 | +10 | +10 | +10 | +10 | Bench mark |

*: Amount required to adjust the pH of the second part to 3.5

TABLE 2

|  | Ex. 6 | Ex. 7 | Ex. 8 | Ex. 9 | Com. Ex. 1 |
|---|---|---|---|---|---|
| First part (% by mass) | | | | | |
| p-Aminophenol | 0.3 | 0.3 | 0.3 | 0.3 | 0.3 |
| m-Aminophenol | 0.1 | 0.1 | 0.1 | 0.1 | 0.1 |
| p-Amino-o-cresol | 0.3 | 0.3 | 0.3 | 0.3 | 0.3 |
| Toluene-2,5-diamine | 0.9 | 0.9 | 0.9 | 0.9 | 0.9 |
| Resorcinol | 0.8 | 0.8 | 0.8 | 0.8 | 0.8 |
| Aqueous ammonia (28% by mass) | 3.0 | 3.0 | 3.0 | 3.0 | 3.0 |
| Ethanolamine | 1.0 | 1.0 | 1.0 | 1.0 | 1.0 |
| Ammonium hydrogencarbonate | 2.5 | 2.5 | 2.5 | 2.5 | 2.5 |
| Sodium cocoyl isethionate | 5.0 | — | — | — | — |
| Sodium methyl lauroyl taurate | — | 5.0 | — | — | — |
| Disodium lauryl sulfosuccinate | — | — | 5.0 | — | — |
| Sodium olefin (C14 to C16) sulfonate | — | — | — | 5.0 | — |
| Sodium laureth sulfate | — | — | — | — | 5.0 |
| Ethanol | 10.0 | 10.0 | 10.0 | 10.0 | 10.0 |
| Propylene glycol | 4.0 | 4.0 | 4.0 | 4.0 | 4.0 |
| EDTA-4Na | 0.1 | 0.1 | 0.1 | 0.1 | 0.1 |
| Ascorbic acid | 0.4 | 0.4 | 0.4 | 0.4 | 0.4 |
| Anhydrous sodium sulfite | 0.5 | 0.5 | 0.5 | 0.5 | 0.5 |
| Perfume | 0.5 | 0.5 | 0.5 | 0.5 | 0.5 |
| Water | Balance | Balance | Balance | Balance | Balance |
| Second part (% by mass) | | | | | |
| Aqueous hydrogen peroxide solution (35% by mass) | 16.3 | 16.3 | 16.3 | 16.3 | 16.3 |
| Sodium cocoyl isethionate | 5.0 | — | — | — | — |
| Sodium methyl lauroyl taurate | — | 5.0 | — | — | — |
| Disodium lauryl sulfosuccinate | — | — | 5.0 | — | — |
| Sodium olefin (C14 to C16) sulfonate | — | — | — | 5.0 | — |
| Sodium laureth sulfate | — | — | — | — | 5.0 |
| Cetanol | 0.6 | 0.6 | 0.6 | 0.6 | 0.6 |
| Etidronic acid | 0.08 | 0.08 | 0.08 | 0.08 | 0.08 |
| Aqueous sodium hydroxide solution (48% by mass) | * | * | * | * | * |
| water | balance | balance | balance | balance | balance |
| Applicability of foam | +9 | +9 | +8 | +7 | Bench mark |
| Compatibility of foam | +10 | +10 | +10 | +8 | Bench mark |

*Amount required to adjust the pH of the second part to 3.5

|  | Ex. | | | Com. Ex. |
| --- | --- | --- | --- | --- |
|  | 10 | 11 | 12 | 1 |
| First part (% by mass) | | | | |
| p-Aminophenol | 0.3 | 0.3 | 0.3 | 0.3 |
| m-Aminophenol | 0.1 | 0.1 | 0.1 | 0.1 |
| p-Amino-o-cresol | 0.3 | 0.3 | 0.3 | 0.3 |
| Toluene-2,5-diamine | 0.9 | 0.9 | 0.9 | 0.9 |
| Resorcinol | 0.8 | 0.8 | 0.8 | 0.8 |
| Aqueous ammonia (28% by mass) | 3.0 | 3.0 | 3.0 | 3.0 |
| Ethanolamine | 1.0 | 1.0 | 1.0 | 1.0 |
| Ammonium hydrogencarbonate | 2.5 | 2.5 | 2.5 | 2.5 |
| Potassium lauryl phosphate | 5.0 | — | — | — |
| Potassium alkyl ($C_9$ to $C_{15}$) phosphate | — | 5.0 | — | — |
| Sodium oleth-10 phosphate | — | — | 5.0 | — |
| Sodium laureth sulfate | — | — | — | 5.0 |
| Ethanol | 10.0 | 10.0 | 10.0 | 10.0 |
| Propylene glycol | 4.0 | 4.0 | 4.0 | 4.0 |
| EDTA-4Na | 0.1 | 0.1 | 0.1 | 0.1 |
| Ascorbic acid | 0.4 | 0.4 | 0.4 | 0.4 |
| Anhydrous sodium sulfite | 0.5 | 0.5 | 0.5 | 0.5 |
| Perfume | 0.5 | 0.5 | 0.5 | 0.5 |
| Water | Balance | Balance | Balance | Balance |
| Second part (% by mass) | | | | |
| Aqueous hydrogen peroxide Solution (35% by mass) | 16.3 | 16.3 | 16.3 | 16.3 |
| Potassium lauryl phosphate | 5.0 | — | — | — |
| Potassium alkyl (C9 to C15) phosphate | — | 5.0 | — | — |
| Sodium oleth-10 phosphate | — | — | 5.0 | — |
| Sodium laureth sulfate | — | — | — | 5.0 |
| Cetanol | 0.6 | 0.6 | 0.6 | 0.6 |
| Etidronic acid | 0.08 | 0.08 | 0.08 | 0.08 |
| Aqueous sodium hydroxide solution (48% by mass) | * | * | * | * |
| Water | Balance | Balance | Balance | Balance |
| Applicability of foam | +10 | +10 | +9 | Bench mark |
| Compatibility of foam | +10 | +10 | +10 | Bench mark |

*Amount required to adjust the pH of the second part to 3.5

Since in Examples 1 to 12, each bubble composing the foam was small in size and the foam was stable compared with that in Comparative Example 1 when discharged onto the hand palm, as shown in Tables 1 to 3, the foam was easy to apply to the hair, was spread well over the hair and was hard to drip, in short, it was compatible to the hair. Furthermore, ΔE was in all of Examples 1 to 12 and Comparative Example 1 within the range of 61±1, indicating the equivalent dyeability.

Example 13

| (First part) | (% by mass) |
| --- | --- |
| Aqueous ammonia (28% by mass) | 3.0 |
| Ethanolamine | 1.5 |
| Ammonium hydrogencarbonate | 0.3 |
| Decyl glucoside | 4.0 |
| Sodium laureth-6 acetate | 4.0 |
| Potassium myristate | 0.1 |
| Laureth-20 | 2.0 |
| Myristyl alcohol | 0.2 |
| Propylene glycol | 4.0 |
| Ethanol | 9.5 |
| Perfume | 0.5 |
| Purified water | balance |

| (Second part) | (% by mass) |
| --- | --- |
| Aqueous hydrogen peroxide solution (35% by mass) | 16.3 |
| Sodium N-lauroyl-N-methyl-β-alanine | 0.5 |
| Cetanol | 0.5 |
| Etidronic acid | 0.1 |
| Aqueous sodium hydroxide solution (48% by mass) | Amount required to adjust pH to 3.5 |
| Purified water | balance |

The semi-long hair of the 20s-age female, test subject was dyed as follows. The first part and the second part of the two-part hair dye according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the hair, which was repeated until 80 g was applied all over the hair previously dried. After completion of the application, the refoaming was carried out with fingers for 20 sec., then the foam was left on the hair at room temperature for 30 min., then the hair was washed, shampooed, rinsed and dried.

Thereby the discharged foam was uniform and fine, was smoothly applicable and compatible to the hair without dripping. The applied foam gave substantially no irritating feeling to the scalp while being left on the hair, and no bleaching unevenness. The whole hair was quasi uniformly bleached.

Example 14

| (First part) | (% by mass) |
| --- | --- |
| Aqueous ammonia (28% by mass) | 3.0 |
| Ethanolamine | 1.5 |
| Ammonium hydrogencarbonate | 0.3 |
| p-Phenylenediamine | 0.1 |
| p-Aminophenol | 0.2 |
| p-Amino-o-cresol | 0.4 |
| Decyl glucoside | 4.0 |
| Sodium laureth-11 acetate | 4.0 |
| Laureth-20 | 2.0 |
| Myristyl alcohol | 0.2 |
| Propylene glycol | 4.0 |
| Ethanol | 9.5 |
| Perfume | 0.5 |
| Purified water | balance |

| (Second part) | (% by mass) |
|---|---|
| Aqueous hydrogen peroxide solution (35% by mass) | 16.3 |
| Sodium cocoyl glutamate | 0.5 |
| Cetanol | 0.5 |
| Etidronic acid | 0.1 |
| Aqueous sodium hydroxide solution (48% by mass) | Amount required to adjust pH to 3.5 |
| Purified water | balance |

The semi-long hair of the 20s-age female, test subject was dyed as follows. The first part and the second part of the two-part hair dye according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the hair and refoamed at the applied region for 2 sec., which procedure was repeated until 80 g was applied all over the hair previously dried. After completion of the application, the refoaming was carried out for the whole hair with fingers for 15 sec., then the foam was left on the hair at room temperature for 20 min., then the hair was washed, shampooed, rinsed and dried.

Thereby the discharged foam was uniform and fine, was smoothly applicable and compatible to the hair without dripping. The applied foam gave substantially no irritating feeling to the scalp while being left on the hair, and no dyeing unevenness. The whole hair was quasi uniformly dyed.

Example 15

| (First part) | (% by mass) |
|---|---|
| Aqueous ammonia (28% by mass) | 3.0 |
| Ethanolamine | 1.5 |
| Ammonium hydrogencarbonate | 0.3 |
| Decyl glucoside | 4.0 |
| Sodium olefin (C14 to C16) sulfonate | 4.0 |
| Laureth-20 | 2.0 |
| Myristyl alcohol | 0.2 |
| Propylene glycol | 4.0 |
| Ethanol | 9.5 |
| Perfume | 0.5 |
| Purified water | balance |

| (Second part) | (% by mass) |
|---|---|
| Aqueous hydrogen peroxide solution (35% by mass) | 16.3 |
| Sodium cocoyl isethionate | 0.5 |
| Cetanol | 0.5 |
| Etidronic acid | 0.1 |
| Aqueous sodium hydroxide solution (48% by mass) | Amount required to adjust pH to 3.5 |
| Purified water | balance |

The semi-long hair of the 20s-age female, test subject was dyed as follows. The first part and the second part of the two-part hair dye according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the hair, which was repeated until 80 g was applied all over the hair previously dried. After completion of the application, the refoaming was carried out with fingers for 20 sec., then the foam was left on the hair at room temperature for 30 min., then the hair was washed, shampooed, rinsed and dried.

Thereby the discharged foam was uniform and fine, was smoothly applicable and compatible to the hair without dripping. The applied foam gave substantially no irritating feeling to the scalp while being left on the hair, and no bleaching unevenness. The whole hair was quasi uniformly bleached.

Example 16

| (First part) | (% by mass) |
|---|---|
| Aqueous ammonia (28% by mass) | 3.0 |
| Ethanolamine | 1.5 |
| Ammonium hydrogencarbonate | 0.3 |
| p-Phenylenediamine | 0.1 |
| p-Aminophenol | 0.2 |
| p-Amino-o-cresol | 0.4 |
| Decyl glucoside | 4.0 |
| TEA dodecylbenzenesulfonate | 4.0 |
| Laureth-20 | 2.0 |
| Myristyl alcohol | 0.2 |
| Propylene glycol | 4.0 |
| Ethanol | 9.5 |
| Perfume | 0.5 |
| Purified water | balance |

| (Second part) | (% by mass) |
|---|---|
| Aqueous hydrogen peroxide solution (35% by mass) | 16.3 |
| Sodium cocoyl taurate | 0.5 |
| Cetanol | 0.5 |
| Etidronic acid | 0.1 |
| Aqueous sodium hydroxide solution (48% by mass) | Amount required to adjust pH to 3.5 |
| Purified water | balance |

The semi-long hair of the 20s-age female, test subject was dyed as follows. The first part and the second part of the two-part hair dye according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the hair and refoamed at the applied region for 2 sec. with fingers, which procedure was repeated until 80 g was applied all over the hair previously dried. After completion of the application, the refoaming was carried out with fingers for 20 sec., then the foam was left on the hair at room temperature for 25 min., then the hair was washed, shampooed, rinsed and dried.

Thereby the discharged foam was uniform and fine, was smoothly applicable and compatible to the hair without dripping. The applied foam gave substantially no irritating feeling to the scalp while being left on the hair, and no dyeing unevenness. The whole hair was quasi uniformly dyed.

Example 17

| (First part) | (% by mass) |
| --- | --- |
| Aqueous ammonia (28% by mass) | 3.0 |
| Ethanolamine | 1.5 |
| Ammonium hydrogencarbonate | 0.3 |
| Decyl glucoside | 4.0 |
| Potassium alkyl ($C_9$ to $C_{15}$) phosphate | 4.0 |
| Laureth-20 | 2.0 |
| Myristyl alcohol | 0.2 |
| Propylene glycol | 4.0 |
| Ethanol | 9.5 |
| Perfume | 0.5 |
| Purified water | balance |

| (Second part) | (% by mass) |
| --- | --- |
| Aqueous hydrogen peroxide solution (35% by mass) | 16.3 |
| Potassium alkyl (C9 to C15) phosphate | 0.5 |
| Cetanol | 0.5 |
| Etidronic acid | 0.1 |
| Aqueous sodium hydroxide solution (48% by mass) | Amount required to adjust pH to 3.5 |
| Purified water | balance |

The semi-long hair of the 20s-age female, test subject was dyed as follows. The first part and the second part of the two-part hair dye according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the hair, which was repeated until 80 g was applied all over the hair previously dried. After completion of the application, the refoaming was carried out with fingers for 20 sec., then the foam was left on the hair at room temperature for 30 min., then the hair was washed, shampooed, rinsed and dried.

Thereby the discharged foam was uniform and fine, was smoothly applicable and compatible to the hair without dripping. The applied foam gave substantially no irritating feeling to the scalp while being left on the hair, and no bleaching unevenness. The whole hair was quasi uniformly bleached.

Example 18

| (First part) | (% by mass) |
| --- | --- |
| Aqueous ammonia (28% by mass) | 3.0 |
| Ethanolamine | 1.5 |
| Ammonium hydrogencarbonate | 0.3 |
| p-Phenylenediamine | 0.1 |
| p-Aminophenol | 0.2 |
| p-Amino-o-cresol | 0.4 |
| Decyl glucoside | 4.0 |
| Laureth-2 phosphate | 4.0 |
| Laureth-20 | 2.0 |
| Myristyl alcohol | 0.2 |
| Propylene glycol | 4.0 |
| Ethanol | 9.5 |
| Perfume | 0.5 |
| Purified water | balance |

| (Second part) | (% by mass) |
| --- | --- |
| Aqueous hydrogen peroxide solution (35% by mass) | 16.3 |
| Laureth-4 phosphate | 0.5 |
| Cetanol | 0.5 |
| Etidronic acid | 0.1 |
| Aqueous sodium hydroxide solution (48% by mass) | Amount required to adjust pH to 3.5 |
| Purified water | balance |

The semi-long hair of the 20s-age female test subject was dyed as follows. The first part and the second part of the two-part hair dye according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the hair and refoamed at the applied region for 2 sec. with fingers, which procedure was repeated until 80 g was applied all over the hair previously dried. After completion of the application, the refoaming was carried out with fingers for 20 sec., then the foam was left on the hair at room temperature for 25 min., then the hair was washed, shampooed, rinsed and dried.

Thereby the discharged foam was uniform and fine, was smoothly applicable and compatible to the hair without dripping. The applied foam gave substantially no irritating feeling to the scalp while being left on the hair, and no dyeing unevenness. The whole hair was quasi uniformly dyed.

Examples 19 to 20 and Comparative Example 2

Each first and second part according to the compositions (% by mass) listed in Table 4 were prepared, contained in vessels respectively, and stored in a thermostatic chamber at 5° C. for 24 hours. Thereafter the vessels were transferred to a room at 20° C., and the first part and the second part were mixed immediately at the mixing ratio (by weight) of 1:1.5 in a squeeze foamer (Daiwa Can Co., internal volume: 150 mL, mesh size: 150 mesh (mixing chamber side), 200 mesh (discharge port side), material: nylon (both)) and discharged in the form of foam. According to the following steps, 80 g of the discharged foam was applied to the whole hair in a dry state of the test subject.

1. To the vessel of the squeeze foamer containing 60 g of the second part, 40 g of the first part was added, and the liquid mixture of the first and second parts is mixed avoiding foaming and the squeeze foamer is mounted.
2. After wearing gloves, the squeeze vessel standing upright is squeezed by one hand to discharge the liquid mixture in the form of foam onto the palm of the other hand.
3. The liquid mixture in the form of foam is applied to the dry hair.
4. Repeating the steps 2 and 3, 80 g of the liquid mixture is applied to the whole hair.
5. The applied liquid mixture is refoamed by massaging the whole hair with fingers for 15 sec.
6. Leave it for 10 min.
7. The applied liquid mixture is refoamed by massaging the whole hair with fingers for 25 sec.
8. After the completion of the refoaming according to the step 7, leave it for 20 min.
9. The whole hair is washed with warm water, followed by shampooing, rinsing and drying successively.

The ratings were determined according to the following criteria and are shown in Table 4 below the composition data.

| Foaming property | |
|---|---|
| A: | Very uniform and fine foam |
| B: | Uniform and fine foam |
| C: | Nonuniform and coarse foam |
| D: | Imperfect foaming with separated water |

Application property (Applicability and compatibility with the hair)

A: Pressing the foam on the hair, the hair dye wets the hair down to the root.

B: By simple hand combing, the hair dye wets the hair root.

C: At some regions, such as a hair-dense region at the back of the head, the hair root can be hardly wetted by the hair dye.

D: Due to poor compatibility, the hair root, etc. cannot be fully wetted by the hair dye.

Foam Stability

A: Very stable foam that lasts while being left.

B: Stable foam that lasts for some time after application.

C: Foam is just stable enough for application, but disappears soon thereafter.

D: Foam disappears soon after discharge, dripping may occur during application.

Dyeing Evenness

A: Dyeable very uniformly without unevenness.

B: Dyeable uniformly with least unevenness.

C: With some dye unevenness.

D: With obvious dye unevenness.

| | | Ex. | | Com. Ex. |
|---|---|---|---|---|
| | | 19 | 20 | 2 |
| First part (% by mass) | | | | |
| p-Aminophenol | | 0.3 | 0.3 | 0.3 |
| m-Aminophenol | | 0.1 | 0.1 | 0.1 |
| p-Amino-o-cresol | | 0.3 | 0.3 | 0.3 |
| Toluene-2,5-diamine | | 0.9 | 0.9 | 0.9 |
| resorcinol | | 0.8 | 0.8 | 0.8 |
| Aqueous ammonia (28% by mass) | | 6.0 | 6.0 | 6.0 |
| Ammonium hydrogencarbonate | | 10.0 | 10.0 | 10.0 |
| Sodium laureth sulfate | | 3.0 | 3.0 | 3.0 |
| Decyl glucoside | | 6.5 | 6.5 | 6.5 |
| Propylene glycol | | 4.0 | 4.0 | 4.0 |
| EDTA-4Na | | 0.1 | 0.1 | 0.1 |
| Ascorbic acid | | 0.4 | 0.4 | 0.4 |
| Anhydrous Na sulfite | | 0.5 | 0.5 | 0.5 |
| Water | | Balance | Balance | Balance |
| Second part (% by mass) | | | | |
| Aqueous hydrogen peroxide solution (35% by mass) | | 16.3 | 16.3 | 16.3 |
| Sodium lauryl sulfate | | 1.0 | 1.0 | 1.0 |
| Lauramide DEA | | 1.8 | — | — |
| Cocamide DEA | | — | 1.8 | — |
| Cetanol | | — | — | 1.8 |
| Oxyquinoline sulfate | | 0.03 | 0.03 | 0.03 |
| Etidronic acid | | 0.08 | 0.08 | 0.08 |
| Aqueous sodium hydroxide solution (48% by mass) | | * | * | * |
| Water | | Balance | Balance | Balance |
| Rating | Foaming property | A | B | D |
| | Application property | A | B | D |
| | Foam stability | A | B | D |
| | Dyeing evenness | A | A | C |

*Amount required to adjust the ph of the second part to 3.5

| Example 21 | |
|---|---|
| (First part) | (% by mass) |
| Aqueous ammonia (28% by mass) | 3.0 |
| Ethanolamine | 1.5 |
| Ammonium hydrogencarbonate | 0.3 |
| Lauryl glucoside | 5.0 |
| Sodium olefin (C14 to C16) sulfonate | 1.0 |
| Sodium laureth-2 sulfate | 1.0 |
| Laureth-23 | 2.0 |
| Lauramide DEA | 3.0 |
| Propylene glycol | 4.0 |
| Ethanol | 9.5 |
| Perfume | 0.5 |
| Purified water | balance |

| (Second part) | (% by mass) |
|---|---|
| Aqueous hydrogen peroxide solution (35% by mass) | 16.3 |
| Sodium cocoyl isethionate | 0.5 |
| Oleamide DEA | 1.0 |
| Etidronic acid | 0.1 |
| Aqueous sodium hydroxide solution (48% by mass) | Amount required to adjust pH to 3.5 |
| Purified water | balance |

The semi-long hair of the 20s-age female test subject was dyed as follows. The first part and the second part for two-part hair dyeing according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the hair, which was repeated until 80 g was applied all over the hair previously dried. After completion of the application, the refoaming was carried out with fingers for 20 sec., then the foam was left on the hair at room temperature for 30 min., then the hair washed, shampooed, rinsed and dried.

Thereby the discharged foam was uniform and fine, was smoothly applicable and compatible to the hair without dripping. The applied foam gave substantially no irritating feeling to the scalp while being left on the hair, and no bleaching unevenness. The whole hair was quasi uniformly bleached.

Example 22

| (First part) | (% by mass) |
| --- | --- |
| Aqueous ammonia (28% by mass) | 3.0 |
| Ethanolamine | 1.5 |
| Ammonium hydrogencarbonate | 0.3 |
| p-Phenylenediamine | 0.1 |
| p-Aminophenol | 0.2 |
| p-Amino-o-cresol | 0.4 |
| Decyl glucoside | 5.0 |
| Sodium laureth sulfate | 3.0 |
| Laureth-23 | 2.0 |
| Cocamide DEA | 3.0 |
| Propylene glycol | 4.0 |
| Ethanol | 9.5 |
| Perfume | 0.5 |
| Purified water | balance |

| (Second part) | (% by mass) |
| --- | --- |
| Aqueous hydrogen peroxide solution (35% by mass) | 16.3 |
| Sodium cocoyl glycinate | 1.0 |
| Lauramidopropyl betaine | 0.1 |
| Lauramide DEA | 1.0 |
| Etidronic acid | 0.1 |
| Aqueous sodium hydroxide solution (48% by mass) | Amount required to adjust pH to 3.5 |
| Purified water | balance |

The semi-long hair of the 20s-age female, test subject was dyed as follows. The first part and the second part for two-part hair dyeing according to the above compositions were prepared and 40 g of the first part and 60 g of the second part were filled in a squeeze foamer vessel (Daiwa Can Co., internal volume: 150 mL, mesh size: 150 mesh (mixing chamber side), 200 mesh (discharge port side), material: nylon (both)) and mixed. The liquid mixture was discharged in the form of foam onto the hand palm with gloves and applied to the hair and refoamed at the applied region for 2 sec. with fingers, which procedure was repeated until 80 g was applied all over the hair previously dried. After completion of the application, the refoaming was carried out with fingers for 20 sec., then the foam was left on the hair at room temperature for 25 min., then the hair was washed, shampooed, rinsed and dried.

Thereby the discharged foam was uniform and fine, was smoothly applicable and compatible to the hair without dripping. The applied foam gave substantially no irritating feeling to the scalp while being left on the hair, and no dyeing unevenness. The whole hair was quasi uniformly dyed.

The invention claimed is:

1. A two-part hair dye comprising a first part containing an alkali agent, a second part containing hydrogen peroxide, and a non-aerosol foamer vessel to discharge in the form of foam a liquid mixture of the first part and the second part, wherein the liquid mixture comprises an anionic surfactant selected from the following components (A):
    (A) a carboxylate type anionic surfactant selected from salts of a $C_8$ to $C_{22}$ fatty acid;
    and wherein the content of component (A) in the first part or the second part is 0.1 to 30% by mass.

2. The two-part hair dye according to claim 1, wherein the carboxylate type anionic surfactant selected from salts of a $C_8$ to $C_{22}$ fatty acid is a basic salt of a single fatty acid selected from lauric acid, myristic acid, palmitic acid, isostearic acid and oleic acid, or a basic salt of a fatty acid mixture selected from coconut oil fatty acid and tallow fatty acid.

3. The two-part hair dye according to claim 1, wherein the carboxylate type anionic surfactant selected from salts of a $C_8$ to $C_{22}$ fatty acid is lauric acid, myristic acid, palmitic acid and oleic acid.

4. The two-part hair dye according to claim 1, wherein the content of the components (A) in the first or second parts is 0.1 to 20% by mass.

5. The two-part hair dye according to claim 1, wherein the content of the components (A) in the first or second parts is 0.1 to 10% by mass.

6. The two-part hair dye according to claim 1, wherein the content of the components (A) in the liquid mixture of the first and second parts is 0.01 to 20% by mass.

7. The two-part hair dye according to claim 1, wherein the content of the components (A) in the liquid mixture of the first and second parts is 0.01 to 10% by mass.

8. The two-part hair dye according to claim 1, wherein the content of the components (A) in the liquid mixture of the first and second parts is 0.01 to 7% by mass.

9. The two-part hair dye according to claim 1, wherein the liquid mixture of the first part and the second part further comprises a higher alcohol.

10. The two-part hair dye according to claim 9, wherein the higher alcohol has a $C_{10}$ to $C_{30}$ alkyl or alkenyl group.

11. The two-part hair dye according to claim 9, wherein the higher alcohol has a $C_{12}$ to $C_{24}$ alkyl or alkenyl group.

12. The two-part hair dye according to claim 9, wherein the higher alcohol has a $C_{14}$ to $C_{22}$ alkyl or alkenyl group.

13. The two-part hair dye according to claim 9, wherein the higher alcohol has a linear alkyl group.

14. The two-part hair dye according to claim 9, wherein the higher alcohol is selected from myristyl alcohol, cetanol, stearyl alcohol, arachyl alcohol, behenyl alcohol and oleyl alcohol.

15. The two-part hair dye according to claim 9, wherein the content of the higher alcohol in the liquid mixture of the first and second parts is 0.01 to 1% by mass.

16. The two-part hair dye according to claim 9, wherein the content of the higher alcohol in the liquid mixture of the first and second parts is 0.1 to 0.8% by mass.

17. The two-part hair dye according to claim 9, wherein the content of the higher alcohol in the liquid mixture of the first and second parts is 0.2 to 0.7% by mass.

18. The two-part hair dye according to claim 9, wherein the content of the higher alcohol in the liquid mixture of the first and second parts is 0.3 to 0.6% by mass.

19. The two-part hair dye according to claim 1, wherein the liquid mixture of the first part and the second part further contains a nonvolatile hydrophilic solvent.

20. The two-part hair dye according to claim 19, wherein the nonvolatile hydrophilic solvent is polyols or $C_1$ to $C_4$ lower alkyl ethers thereof.

21. The two-part hair dye according to claim 19, wherein the nonvolatile hydrophilic solvent is glycerin, diglycerin, propylene glycol, dipropylene glycol, 1,3-butanediol, ethylene glycol, diethylene glycol, isoprene glycol, sorbitol, ethylene glycol monomethyl ether, ethylene glycol monoethyl ether, diethylene glycol monomethyl ether and diethylene glycol monoethyl ether.

22. The two-part hair dye according to claim 19, wherein the content of the nonvolatile hydrophilic solvent in the liquid mixture of the first and second parts is 0.01 to 4% by mass.

23. The two-part hair dye according to claim 19, wherein the content of the nonvolatile hydrophilic solvent in the liquid mixture of the first and second parts is 0.1 to 3% by mass.

24. The two-part hair dye according to claim 19, wherein the content of the nonvolatile hydrophilic solvent in the liquid mixture of the first and second parts is 0.2 to 2% by mass.

25. The two-part hair dye according to claim 1, wherein the viscosity (25° C.) of the liquid mixture of the first and second parts is 1 to 300 mPa·s.

26. The two-part hair dye according to claim 1, wherein the viscosity (25° C.) of the liquid mixture of the first and second parts is 1 to 100 mPa·s.

27. The two-part hair dye according to claim 1, wherein the viscosity (25° C.) of the liquid mixture of the first and second parts is 3 to 100 mPa·s.

28. The two-part hair dye according to claim 1, wherein the viscosity (25° C.) of the liquid mixture of the first and second parts is 3 to 80 mPa·s.

29. The two-part hair dye according to claim 1, wherein the viscosity (25° C.) of the liquid mixture of the first and second parts is 3 to 50 mPa·s.

30. The two-part hair dye according to claim 1, wherein the viscosity (25° C.) of the liquid mixture of the first and second parts is 5 to 50 mPa·s.

31. The two-part hair dye according to claim 1, wherein the viscosity (25° C.) of the liquid mixture of the first and second parts is 5 to 30 mPa·s.

32. The two-part hair dye according to claim 1, wherein the viscosity (25° C.) of the liquid mixture of the first and second parts is 10 to 30 mPa·s.

33. The two-part hair dye according to claim 1, wherein the first part comprises the oxidation dye or the direct dye.

34. A method for dyeing hair, comprising the steps of discharging in the form of foam the liquid mixture in the two-part hair dye according to claim 1 from a non-aerosol foamer vessel; once receiving the foam by hand; and applying the foam to the hair.

35. The method for dyeing hair according to claim 34, wherein a blocking procedure is not conducted.

36. The method for dyeing hair according to claim 34, wherein the applied range of the foam is the entirety of the hair.

37. The method for dyeing hair according to claim 34, wherein the applied foam is foaming up again on the hair.

* * * * *